(12) United States Patent
Trkovnik et al.

(10) Patent No.: US 6,407,073 B1
(45) Date of Patent: Jun. 18, 2002

(54) USE OF COUMARIN DERIVATIVES FOR THE TREATMENT OF DIGESTIVE TRACT DISORDERS

(75) Inventors: Mladen Trkovnik; Miroslav Trkovnik, both of Zagreb (HR)

(73) Assignee: Bio-Monde Preparations Limited (GB)

( * ) Notice: Subject to any disclaimer, the term of this patent is extended or adjusted under 35 U.S.C. 154(b) by 0 days.

(21) Appl. No.: 09/530,973

(22) PCT Filed: Oct. 22, 1998

(86) PCT No.: PCT/GB98/03169

§ 371 (c)(1), (2), (4) Date: Jul. 14, 2000

(87) PCT Pub. No.: WO99/21550

PCT Pub. Date: May 6, 1999

(30) Foreign Application Priority Data

Oct. 24, 1997 (GB) .............................................. 9722600

(51) Int. Cl.$^7$ .......................... A61K 31/35; A61K 31/70
(52) U.S. Cl. .......................... 514/27; 514/456; 514/457
(58) Field of Search .......................... 514/27, 456, 457

(56) References Cited

U.S. PATENT DOCUMENTS

| 3,175,943 A | 3/1965 | Mulho et al. ................ 502/150 |
| 4,241,047 A | 12/1980 | Lechevin et al. .............. 424/33 |
| 5,281,721 A | 1/1994 | Powers et al. ................ 549/23 |

FOREIGN PATENT DOCUMENTS

| EP | 240874 | 10/1987 |
| FR | 2726435 | 5/1996 |

OTHER PUBLICATIONS

Gilani, A. H., et al., Pharmacological Research, vol. 37, No. 1, pp. 31–35 (1998).
Petrioli, G., Fortschr Med 97, 25–26, pp. 1174–1178 (Jul. 5, 1979) and English Translation thereof.
The Merck Index, 12$^{th}$ edition, p. 834, item 4903 (1972).

*Primary Examiner*—Elli Peselev
(74) *Attorney, Agent, or Firm*—Jones,Tullar & Cooper. P.C.

(57) ABSTRACT

A compound of the formula wherein W is H or a β-D-glucopyranoslyloxy group, and Y and Z are independently H, $C_{1-6}$ alkyl, or $C_{1-6}$ alkoxy or a pharmacologically acceptable derivative thereof, is effective in the treatment or prophylaxis of a disorder benefitting from a decrease in the activity or concentration of transaminase enzymes, particularly liver disorders. The compound is preferably administered orally as a dietary supplement in combination with one or more of bee pollen, matricaria camomile, asperula oderata, royal jelly or honey.

9 Claims, No Drawings

USE OF COUMARIN DERIVATIVES FOR THE TREATMENT OF DIGESTIVE TRACT DISORDERS

This Application is a 371 of PCT/GB98/03169 filed Oct. 22, 1998.

The present invention relates to coumarin derivatives, particularly hymecromone, to pharmaceutical compositions containing them and to their use in the treatment of disorders of the liver, kidney, pancreas, bladder and gastro-intestinal tract.

The liver is a complex organ with many diverse functions. It is the central organ of metabolism of carbohydrates, proteins, and fat. It stores glycogen and takes part in regulating blood sugar, and stores other essential substances such as vitamins and factors concerned in haemopoiesis. It synthesises fibrinogen, prothrombin, heparin, and plasma proteins, and is a site of destruction of deteriorated red blood cells. It is also the chief detoxicating organ of the body rendering unwanted substances innocuous.

Viral hepatitis refers to infection of the liver caused by a group of hepatitis viruses. Those so far identified are designated A, B, C, D and E. Other viruses such as Epstein-Barr virus and yellow fever virus may be secondary causes of hepatitis and nonviral infections, drugs, chemicals and alcoholism may also cause hepatitis. One of the main treatments for the various viral hepatitis infections is alpha or beta interferon, but in many cases it is not particularly effective. Other drugs that may produce a therapeutic response include lamivudine, ursodeoxycholic acid and vidarabine.

Primary biliary cirrhosis is a chronic liver disease of unknown aetiology, which develops due to progressive destruction of small and intermediate bile ducts within the liver, subsequently evolving to fibrosis and cirrhosis. Over 90% of patients are female, usually aged between 40 and 60 years. The disease is thought to be autoimmune in nature, perhaps triggered by a micro-organism in the environment and most patients exhibit autoantibodies to mitochondria. The disease is slowly progressive but no specific treatment is available.

Wilson's disease is due to an inborn error of liver metabolism leading to the accumulation of toxic concentrations of copper. Gilbert's syndrome is an inherited disorder that affects the way bilirubin is handled by the liver. Symptoms include mild jaundice, fatigue and abdominal pain. Again in both Wilson's disease and Gilbert's syndrome, there is no real effective treatment.

Accordingly there is a constant need for new compounds to treat the various liver disorders.

The inventor has now found that certain organic compounds (including naturally occurring extracts are effective in the treatment of various liver and other disorders.

Accordingly in a first aspect of the invention there is provided use of a compound of the Formula 2:

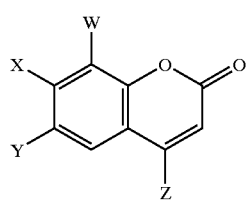

Formula 2 wherein:
W is H or a β-D-glucopyranosyloxy group,
X is OH, and
Y and Z are independently H, $C_{1-6}$ alkyl, or $C_{1-6}$ alkoxy and pharmacologically acceptable derivatives thereof in the manufacture of a medicament for the treatment or prophylaxis of a disease selected from liver, kidney, pancreatic, bladder, and gastro-intestinal disorders and disorders treatable by reducing the concentration or activity of transaminase enzymes, said disease not being treatable with a choleretic or biliary antispasmodic agent.

Preferably Z is methyl.

Examples of known compounds covered by Formula 2 are. as follows: fraxin (7,8-dihydroxy-6-methoxycoumarin-8-β-D-glucoside), umbelliferone (7-hydroxycoumarin), skimmin (7-(glucosyloxy)coumarin), and hymecromone (7-hydroxy-4-methylcoumarin).

All compounds of Formula 2 are hereinafter referred to as "compounds of the invention".

The compound that the inventor has done most work on and which has been found to be particularly effective is hymecromone (CAS Registry no. 90-33-5).

Although hymecromone is primarily used for the fluorometric determination of enzyme activity (Clin. Chim. Acta., 39,49 (1972); Anal. Biochem., 54,40 (1973)) it is also known as a choleretic (agent which aids the excretion of bile) and a biliary antispasmodic, and has been administered in doses of 300 mg–400 mg. (The Merck Index, 12th Edition, 4903 and Martindale, The Extra Pharmacopoeia, 31st Edition p1715). A more soluble form of hymecromone is disclosed in EP-A-0240874, and tablets of hymecromone for improving the excretion of bile are known from U.S. Pat. No. 3,175,943. The choleretic and biliary antispasmodic activity of hymecromone also is referred to in Petrioli (Fortschr. Med. 1979 Jul. 5; 97 (25–26):1174–8) and U.S. Pat. No. 4,241,047.

Hymecromone is commercially available from ABCR GmbH & Co Kg (Karlsruhe, Germany, Acros organics (Geel, Belgium), Loba Feinchemie AG (Fischamend, Austria), Sigma-Aldrich Fine Chemicals (Poole, Dorset, UK). Hymecromone is also available as a natural occurring extract of Manna Ash known as Fraxin.

By pharmacologically acceptable derivatives of the compounds of Formula 2, it is meant to include prodrugs, salts, solvates, esters, ethers, amides, glycosylated derivatives, and including methylated, aminated and acetylated derivatives.

By prodrug is meant any compound, which is capable of being metabolised in vivo to give a compound of Formula 1.

By salt it is meant to include pharmaceutically acceptable salts derived from an appropriate base such as alkali metal salts (e.g. sodium or potassium), alkaline earth metals (e.g. magnesium or calcium), ammonium and $NX_4$(wherein X is $C_{1-4}$ alkyl), or salzs of a hydrogen atom including salts formed from organic and inorganic acids such as those formed from hydrochloric, hydrobromic, sulphuric, citric, tartaric, phosphoric, lactic, pyruvic, acetic, trifluoroacetic, succinic, oxalic, fumaric, maleic, xaloaceltic, methanesulphonic, ethanesulphonic, ρ-toluenesulphonic, benzenesulphonic and isethionic acids.

The compounds of the invention, particularly hymecromone, have hepatoprotective and/or hepatoregenerative properties. Liver disorders which can be treated comprise hepatitis including infective hepatitis (e.g. viral hepatitis of types A, B, C, D and E), chronic active hepatitis, acute infective hepatitis, toxic hepatitis (e.g. as caused by drugs and narcotics X-rays, solvents, chemotherapy, and alcohol abuse), steatosis hepatitis, acute parenchymatous hepatitis, amoebic hepatitis, cytomegalic hepatitis, enzootic hepatitis, familial hepatitis, homologous serum hepatitis, intestitial hepatitis, suppurative hepatitis, and trophopathic hepatitis. Various cirrhosis of the liver conditions which can be treated include primary and secondary biliary cirrhosis, alcoholic cirrhosis, annular cirrhosis, atrophic cirrhosis, bacterial cirrhosis, capsular cirrhosis, cardiac cirrhosis, fatty cirrhosis lymphatic cirrhosis and pigmentary cirrhosis. Yet further liver disorders against which the compounds of the invention are effective are Wilson's disease and Gilbert's svndrome.

The compounds of the invention are particularly effective in protecting the liver from the toxic effects of anabolic steroids, alcohol, chemotherapy, solvents, drugs, and environmental pollution.

Early investigations also suggest that compounds of the invention such as hymecromone will also be effective in the treatment or prophylaxis of disorders of the kidney (e.g. cirrhosis of the kidney), pancreas (e.g. pancreatitis), bladder and castrointestinal tract (e.g. cirrhosis of the stomach).

The invention can also be used to rejuvenate healthy people, especially those ex posed to heavy physical labour, the elderly a nd otherwis e healthy people recovering from illness, and sportsmen (especially those using anabolic steroids).

Without being bound by theory, it is thought that the corpounds of the invention are at least partly effective by reducing the concentration or activity in the peripheral blo od of transaminase enzymes, such as serum glutamic oxaloacetic transaminase (SGOT) or aspartate aminotransferase (AST), serum glutamic pyruvic transaminase (SGPT) or alanine transaminase (ALT), and gamma glutamyl traospe) tidase (GGT).

The invention also provides a composition comprising a compound of Formula 2 in combination with one or more of bee pollen, matricaria camomile, asperula oderata, royal jelly or honey.

The compositions may be presented in unit dose forms containing a predetermined amount of active ingredient per unit dose. Such a unit may contain for example 50 mg to 2000 mg preferably 20 mg to 500 mg depending on the condition being treated, the route of administration and the age, weight and condition of the patient. In the case of a compound of the invention suspenuhed in hney, a unit dosage would be relative to on e or more spoonfuls of the honey. The patient should preferably receive in the region of rug to 50 g per month, advantageously about 25 g to 28 g/month of a compound of the invention. Each unit dose may be administered once, twice, three or more times daily.

The compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

The compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

The compositions adapted forrectal administration may be presented as suppositories or enemas, and those adapted for vacinal administration may be presented as pessaries, tampons, creams, gels, pastes, foams or spray formulations.

The compositions adapted for parenteral administration include aqueous and non-aqueous sterile injection solutions which may contain anti-oxidants, buffers, bacteriostats and solutes which render the formulation isotonic with the blocd cf the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition reau crind only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as hereinabove recited, or an appropriate fraction thereof, of an active ingredient.

In a preferred oral composition, a compound of the invention is present together with one or more of the following other components preferably at the given relative quantities:

| Component | Preferred Range (g) | More Preferred Range (g) |
|---|---|---|
| Compound of the invention (e.g. hymecromone) | 15–30 | 25–28 |
| Bee Pollen | 2 to 10 | About 5 |
| Matricaria Camomile (Camomile) pulv. | 2 to 10 | About 5 |
| Asperula Oderata (Sweet Woodruff) pulv. | 2 to 10 | About 5 |
| Royal Jelly | 5 to 15 | About 10 |

The composition can be suspended in honey and presented as a rejuvenating dietary supplement.

In a particularly preferred oral composition, there is provided a capsule containing from 100 to 300 mg (preferably about 210 mg) of a compound of the invention (e.g. hymecromone), from 3 to 7 mg (preferably about 5 mg) of camomile, and from 3 to 7 mg (preferably about 5 mg) of bee pollen.

The preferred source of a Compound of the invention (hymecromone) is Loba Feinchemie AG (Fischamend, Austria);

The invention will now be illustrated by way of the following Examples.

EXAMPLE 1

A composition of the invention suspended in honey is as follows:

| Ingredient | Weight |
|---|---|
| Bee Pollen | 0.5 g |
| Matricaria Camomile (Camomile) pulv. | 0.5 g |
| Matricaria Camomile (Camomile) extr. sic. | 2.5 g |
| Asperula Oderata (Sweet Woodruff) pulv. | 0.5 g |
| Compound of the invention [Fraxinus Ornus (Manna Ash) extr. sic.] | 2.0 g |
| Bee Honey | 250.0 g |

EXAMPLE 2

A further composition of the invention is as follows:

| Ingredient | Weight |
| --- | --- |
| Bee Pollen | 0.5 g |
| Matricaria Camomile (Camomile) pulv. | 0.5 g |
| Matricaria Camomile (Camomile) extr. sic. | 0.5 g |
| Asperula Oderata (Sweet Woodruff) pulv. | 0.5 g |
| Compound of the invention [4-Methyl-7-hydroxycoumarin (hymecromone)] | 5.0 g |
| Royal Jelly | 1.5 g |
| Bee Honey | 250.0 g |

EXAMPLE 3

A composition of the invention according to Example 1 was administered to 30 patients (20 males and 10 females) over a 3-month period.

During the three months of monitoring, the clinical diagnosis remained constant, however, changes were reported in the biochemical activity, evident in a reduction in enzymatic activities, SGOT (AST) and SGPT (ALT) in 70% of cases, as well as an improvement in symptomatic levels. In 65% of cases, fatigue and overall exhaustion were eliminated. In patients with chronic pancreatitis, pain in the area of the pancreas disappeared and sexual instinct reappeared. During testing there were no harmful side effects present.

EXAMPLE 4

Patient A was diagnosed as having hypertrigliceridaemia. His liver was increased in size for 2p.p. of discrete ehogenous and homogenous parenhim (steatiosis hepatitis). He felt constantly tired, had chest and intestinal rumblings (especially after meals), complained of poor digestion (particularly stomach heaviness after any type of food), and experienced repeated heartburn and belching.

Enzyme Levels: GGT: 90.0; SGPT: 41.3; SGOT: 33.8.

The patient was given a course of a composition of the invention according to Example 1 at 2x5ml spoonfuls, 3 times per day for 40 days (hymecromone content equivalent to 140 mg/5ml spoonful or 25 gms per month). The patient's transaminase levels were then measured again and were found to have decreased as follows: GGT:40.3; SGPT:18.4; SGOT:21.

EXAMPLE 5

Patient B was diagnosed as having steatosis hepatitis (an early stage of hepatitis). Liver size within normal, of ehogenous and homogenous parenhim, which indicates liver steatosis. The patient complained of chronic pains below the right rib. After trying to digest food, he experienced a bloated or heavy stomach and constant belching. He also complained of occasional lethargy.

Biochemical Analysis: GGT:220; SGPT:110; SGOT:65.

After a course of a composition of the invention as in Example 1, the steatosis hepatitis was found to be in regression. The patient's transaminase enzyme levels also decreased as follows: GGT:146; SGPT:26.2; SGOT:24.2.

EXAMPLE 6

Patient C was diagnosed as having laesio hepatitis diffusa chr. and hepatomegalia. The patient had suffered from liver problems for some time, he felt depressed and tired, had a high fever and was jaundiced. He had an enlarged liver of hyperehogenous and inhomogenous parenhim, indicating chronic diffused liver lesion.

Biochemical Analysis: GGT:685; SGPT:113; SGOT:124.

After a course of a composition of the invention as in Example 1, the patient's transaminase enzyme levels decreased as follows: GGT:57; SGPT:27.3; SGOT:23.9.

EXAMPLE 7

The preparation of Example 2 was used in the treatment of several patients suffering from various kinds of liver disease, some very advanced, but in all cases showing high levels of enzymes, particularly transaminase enzymes.

In all cases, the patients received the preparation of the invention in addition to the standard treatments (e.g. B-vitamins, K-vitamins, Paraaminometilbenzoic acid, fursemid, aldactone, propranolol and others). Pains found under the right ribs, bend, fatigue and general exhaustion were the predominant complaints of the patients.

Liver Profile, Blood Analysis and general health conditions were monitored on a monthly basis.

The following enzymes were measured in the biochemical analysis:

Serum Glutamic Oxaloacetic Transaminase (SGOT) or aspartate aminotransferase (AST): (NORMAL VALUE: 10 to 40 international units per decilitre);

Serum Glutamic Pyruvic Transaminase (SGPT) or alanine transaminase (ALT): (NORMAL VALUE: 10 to 30 international units per decilitre);

Gamma Glutamyl Transpeptidase (GGT): (NORMAL VALUE: 0–45 international units per decilitre).

On the basis of the biochemical determination, the patients were classified into four groups.

GROUP 1: Patients diagnosed with: cirrhosis and chronic active hepatitis, with high transaminase (AST [SGOT] & ALT [SGPT] over 120);

GROUP 2: Patients diagnosed with: viral hepatitis (chronic), both B and C chronic type in active state (AST [SGOT] and ALT [SGPT] over 200);

GROUP 3: Patients diagnosed with: toxic alcoholic liver lesion in acute state, with high transaminase (AST [SGOT] and ALT [SGPT] over 350), acute alcoholic hepatitis;

GROUP 4: Patients diagnosed with: syndromes and high transaminase.

In summary, the patients, who were using the composition of the invention for more than two months in conjunction with standard therapy, recovered quicker and felt much better. In addition to an improved general state of health, the patients reported improvements in appetite and physical fitness.

The biochemical analysis showed a rapid reduction of blood transaminase (AST [SGPT] and ALT [SGOT] to 100 units or less.

Patients in the first (1) third (3) and fourth (4) group responded better and quicker when using the invention and the transaminase fell quickly to between 60 and 80.

The patients in the second (2) group, those with chronic B or C hepatitis, whether receiving Interferon or not, responded slower. Initially there was no physical signs of improvement, but after a time a reduction in transaminase concentration in blood (AST [SCOT] and ALT [SGPT]), was noticed concomitant with regression of the disease.

EXAMPLE 8

The hepatoprotective effect of a composition in accordance with the invention was investigated in mice with acetaminophen (paracetamol) induced hepatotoxicity.

CBA/H Zgr inbred mice were raised in an animal colony unit. Mice of both sexes aged 3 to 4 month were used in the experiments. Mice were maintained under standard laboratory conditions, fed with commercially available murine food pellets and allowed water ad libitum.

The procedure of Guarner was followed (see Hepatology 1988; 3:248–53). To induce hepatic drug-metabolising enzymes, mice were given phenobarbitone-sodium in drinking water for 7 days (0.3 g/L). Thereafter, mice were fasted overnight.

Three different doses (10, 50 or 250 mg/kg) of a Composition of the invention (Hymecromone) were given to mice intraperitoneally in volumes of 0.5 ml 30 minutes before intragastric administration of acetaminophen (300 mg/kg).

The above ingredients were dissolved in phosphate buffered saline (PBS) to which several drops of Tween 20™ (polyoxyethylene 20 sorbitan monolaurate) were added (50 μl/ml). The resulting white milk suspension was administered to mice intraperitoneally.

At the same time, control animals were given 0.5 ml of pyrogen-free saline to which several drops of Tween 20™ (50 μl/ml) were added.

Acetaminophen, dissolved in heated PBS, was given intragastrically, by stomach tube, in a volume of 0.5 ml. Animals were allowed food 4 hours later. Mortality of mice was followed for 48 hours, as previous results have shown that control mice (given saline rather than the composition before acetaminophen) either die within this period or fully recover and survive indefinitely.

Plasma aspartate aminotransferase (AST) and alanine aminotransferase (ALT) were measured 24 hours after the administration of acetaminophen, because it has been observed that the levels of AST and ALT are at their peak values at this time. Mice were given 250 units of Hymecromone intraoeritoneally 15 minutes before bleeding. Blood was obtained by puncture of medial orbital angle using glass capillary tubes. Plasma was stored at −20° C. until aminotransferase determination, which was carried out using standard laboratory techniques (see Expert Panel on Enzymes, Committee on Standards, Clin. Chem. Biochem. 1977; 15: 39–51 and Clin. Chem. Acta. 1980; 105: 147F–54F).

Differences in survival between groups of mice were compared by $\chi^2$-test. Plasma AST and ALT concentrations are expressed as means±SEM and differences between groups were compared by Student's t-test.

Table 1 shows the mortality of mice 48 hours after acetaminophen administration. In comparison with the control group of mice given saline, pretreatment of mice with 250 mg/kg of Hymecromone significantly reduced the mortality of mice (P<0.01). The mortality of mice given 10 or 50 mg/kg of the composition was similar to that observed in control mice given saline. Tables 2 and 3 show the mortality of mice of two further experiments. As shown, pretreatment of mice with Hymecromone (250 mg/kg) statistically significantly reduced the mortality of mice in comparison with control mice given saline (P<0.001).

TABLE 1

The effect of different doses of Hymecromone on survival of mice with AAP-induced hepatotoxicity

| Treatment[a] | Dose of Hymecromone (mg/kg) | No of dead mice/ Total No of mice (%)[b] |
|---|---|---|
| Saline + AAP | — | 13/13 (100) |
| Hymecromone + AAP | 10 | 12/12 (100) |
| Hymecromone + AAP | 50 | 11/12 (92) |
| Hymecromone + AAP | 250 | 2/7 (29)[c] |

[a]Mice were given 300 mg/kg AAP intragastrically in volume of 0.5 ml. Saline or different doses of Hymecromone were given intraperitoneally 30 minutes before AAP administration
[b]Mortality was recorded 48 hours after AAP administration
[c]Significantly different in relation to the control group of mice treated with saline (P < 0.01)

TABLE 2

The effect of different doses of Hymecromone on survival of mice with AAP-induced hepatotoxicity

| Treatment[a] | Dose of Hymecromone (mg/kg) | No of dead mice/ Total No of mice (%)[b] |
|---|---|---|
| Saline + AAP | — | 10/13 (77) |
| Hymecromone + AAP | 50 | 9/13 (93) |
| Hymecromone + AAP | 250 | 0/13 (0)[c] |

[a]Mice were given 250 mg/kg AAP intragastrically in volume of 0.5 ml. Saline or Hymecromone were given intraperitoneally 30 minutes before AAP administration.
[b]Mortality was recorded 48 hours after AAP administration.
[c]Significantly different in relation to the control group of mice treated with saline (P < 0.001).

TABLE 3

The effect of Hymecromone on survival of mice with AAP-induced hepatotoxicity

| Treatment[a] | No of dead mice/ Total No of mice (%)[b] |
|---|---|
| Saline + AAP | 16/16 (100) |
| Hymecromone + AAP | 0/15 (0)[c] |

[a]Mice were given 250 mg/kg AAP intragastrically in volume of 0.5 ml. Saline or Hymecromone (250 mg/kg) were given intraperitoneally 30 minutes before AAP administration.
[b]Mortality was recorded 48 hours after AAP administration.
[c]Significantly different in relation to the control group of mice treated with saline (P < 0.001)

EXAMPLE 9

The effect of a Compound of the invention (Hymecromone) was investigated on plasma aminotransferase levels in mice with AAP-induced hepatotoxicity.

Hymecromone (250 mg/kg) or a control of saline was given to mice 30 minutes before administration of acetaminophen (220 mg/kg). Plasma AST and ALT were measured 24 hours after acetaminophen administration. Table 4 shows plasma aminotransferase levels in normal and in mice treated with Hymecromone or saline. As shown, in comparison with normal mice, the administration of acetaminophen increased AST and ALT by approximately 19 and 100 times, respectively. Pretreatment of mice with the composition significantly reduced the increase of AST and ALT in comparison with control mice pretreated with saline (AST five times and ALT three times; P<0.005).

TABLE 4

Plasma aminotransferase levels in mice with AAP-induced hepatotoxicity pretreated with saline or Hymecromone

| Treatment[a] | AST (U/L)[b] | ALT(U/L)[b] |
|---|---|---|
| Normal mice | 75 ± 4 | 23 ± 1 |
|  | (n = 19) | (n = 19) |
| Saline + AAP | 1417 ± 355 | 2300 ± 376 |
|  | (n = 16) | (n = 16) |
| Hymecromone + AAP | 267 ± 56[c] | 776 ± 166[c] |
|  | (n = 16) | (n = 16) |

[a]Saline or Hymecromone (250 mg/kg) were given 30 minutes before AAP administration (220 mg/kg)
[b]Determined 24 hours after AAP administration; mean ± SEM
[c]Significantly different in relation to the control group of mice given saline before AAP administration (P < 0.005)

The results of the investigation have shown that the composition in accordance with the invention has hepatoprotective effect in mice with acetaminophen-induced acute hepatotoxicity. The composition in a dose of 250 mg/kg given intraperitoneally to mice 30 minutes before administration of acetaminophen, significantly reduced the mortality of mice and reduced plasma aminotransferase levels in comparison with control mice given saline before administration of acetaminophen.

The invention is therefore very effective in the treatment of different kinds of liver, kidney, pancreatic and gastrointestinal disorders. It reduces the transaminase levels in peripheral blood, and reduces the activity and aggressiveness of the illness.

What is claimed is:

1. A method for the treatment of hepatotoxicity not being accompanied by a deficiency in bile excretion or biliary spasms, in a patient having hepatotoxicity not accompanied by a deficiency in bile excretion or biliary spasms, which method comprises administering to said patient a transaminase enzyme reducing amount of a compound of Formula 2:

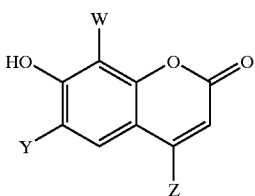

Formula 2 wherein:

W is H or a β-D-glucopyranosyloxy group; and

Y and Z are independently H, $C_{1-6}$ alkyl or $C_{1-6}$ alkoxy; or pharmacologically acceptable derivatives thereof.

2. A method according to claim 1, wherein the compound of Formula 2 is hymecromone.

3. A method for the treatment of liver disorders treatable by a decrease in the activity or concentration of transaminase enzymes, said disorders not being accompanied by a deficiency in bile excretion or biliary spasms, in a patient having a liver disorder treatable by a decrease in the activity or concentration of transaminase enzymes not accompanied by a deficiency in bile excretion or biliary spasms, which method comprises administering to said patient a transaminase enzyme reducing amount of a compound of Formula 2:

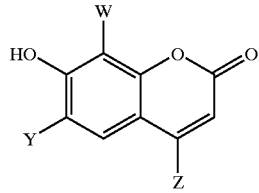

Formula 2 wherein:

W is H or a β-D-glucopyranosyloxy group; and

Y and Z are independently H, $C_{1-6}$ alkyl or $C_{1-6}$ alkoxy; or pharmacologically acceptable derivatives thereof.

4. A method according to claim 3, wherein the compound of Formula 2 is hymecromone.

5. A method according to claim 4, wherein the liver disorder is resultant from chemotherapy.

6. A method according to claim 4, wherein the liver disorder is cirrhosis.

7. A method according to claim 4, wherein the liver disorder is hepatitis.

8. A method for the treatment of disorders treatable by a decrease in the activity or concentration of transaminase enzymes, said disorders not being accompanied by a deficiency in bile excretion or biliary spasms, in a patient having a disorder treatable by a decrease in the activity or concentration of transaminase enzymes not accompanied by a deficiency in bile excretion or biliary spasms, which method comprises administering to said patient a transaminase enzyme reducing amount of a compound of Formula 2:

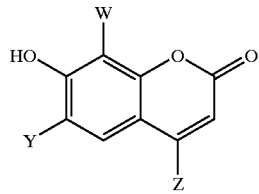

Formula 2 wherein:

W is H or a β-D-glucopyranosyloxy group; and

Y and Z are independently H, $C_{1-6}$ alkyl or $C_{1-6}$ alkoxy; or pharmacologically acceptable derivatives thereof.

9. A method according to claim 8, wherein the compound of Formula 2 is hymecromone.

* * * * *